(12) United States Patent
De Munck et al.

(10) Patent No.: US 8,968,671 B2
(45) Date of Patent: Mar. 3, 2015

(54) MIXING IN OXIDATION TO PHTHALIC ANHYDRIDE

(75) Inventors: Nicolaas Anthony De Munck, Barendrecht (NL); Aad Gerrit Oskam, Rozenburg ZH (NL); Johnny Jozef Houben, Rotterdam (NL); Evert C. Klein, Dorst (NL)

(73) Assignee: ExxonMobil Chemical Patents Inc., Hosuton, TX (US)

(*) Notice: Subject to any disclaimer, the term of this patent is extended or adjusted under 35 U.S.C. 154(b) by 1348 days.

(21) Appl. No.: 12/673,396

(22) PCT Filed: Sep. 9, 2008

(86) PCT No.: PCT/EP2008/061932
§ 371 (c)(1),
(2), (4) Date: Apr. 28, 2011

(87) PCT Pub. No.: WO2009/040245
PCT Pub. Date: Apr. 2, 2009

(65) Prior Publication Data
US 2011/0196159 A1    Aug. 11, 2011

(30) Foreign Application Priority Data
Sep. 28, 2007 (GB) .................................. 0718994.7

(51) Int. Cl.
*B01F 15/06* (2006.01)
*B01F 3/04* (2006.01)
(Continued)

(52) U.S. Cl.
CPC ............. *C07C 67/08* (2013.01); *B01F 3/04049* (2013.01); *B01F 5/0453* (2013.01); *B01F 5/0456* (2013.01); *B01F 5/0463* (2013.01); *B01J 4/002* (2013.01); *B01J 8/065* (2013.01); *B01J 8/067* (2013.01); *C07C 51/265* (2013.01); *C07C 67/303* (2013.01); *C07D 307/89* (2013.01); *B01J 2208/00849* (2013.01); *C07C 2101/14* (2013.01)
USPC ........... 422/224; 261/128; 261/115; 366/144; 366/148

(58) Field of Classification Search
USPC .................. 366/147, 144, 148; 261/115, 128; 422/224
See application file for complete search history.

(56) References Cited

U.S. PATENT DOCUMENTS

| 2,310,907 A | 2/1943 | McMillan |
| 4,647,436 A | 3/1987 | Herbort et al. |
| 6,984,289 B2 | 1/2006 | Domes et al. |
| 2003/0013931 A1 | 1/2003 | Block et al. |

FOREIGN PATENT DOCUMENTS

| DE | 20 2005 012 725 | 11/2005 |
| DE | 10 2004 052 827 | 5/2006 |

(Continued)

*Primary Examiner* — T. Victor Oh
(74) *Attorney, Agent, or Firm* — Luke A. Parsons; Leandro Arechederra, III

(57) ABSTRACT

A system for mixing ortho-xylene with an oxygen-containing gas such as air comprises an evaporator vessel fed with the gas and having a lance projecting into the gas. The lance is provided with a metal spray nozzle for injecting droplets of hot liquid ortho-xylene into the gas stream, concurrently with the direction of flow of the gas. The metal at the surface of the spray nozzle, that in use is in contact with the liquid ortho-xylene, has a high surface hardness to resist erosion, particularly by cavitation. The system is useful in the production of phthalic anhydride by the oxidation of ortho-xylene with air, whereby the risk for deflagrations is reduced. A soft metal seal is the preferred gasket between the spray nozzle and the lance.

9 Claims, 8 Drawing Sheets

(51) Int. Cl.
*B01J 19/00* (2006.01)
*C07C 67/08* (2006.01)
*B01F 5/04* (2006.01)
*B01J 4/00* (2006.01)
*B01J 8/06* (2006.01)
*C07C 51/265* (2006.01)
*C07C 67/303* (2006.01)
*C07D 307/89* (2006.01)

(56) References Cited

FOREIGN PATENT DOCUMENTS

| | | | |
|---|---|---|---|
| DE | 102004052827 | * | 5/2006 |
| EP | 1 273 919 | | 7/2003 |
| GB | 1 403 451 | | 8/1975 |
| JP | 56-144087 | | 11/1981 |
| WO | WO2009/402046 | | 4/2009 |

* cited by examiner

MIXING IN OXIDATION TO PHTHALIC ANHYDRIDE

PRIORITY CLAIM

This application is a 371 National Stage Application of International Application No. PCT/EP2008/061932, filed Sep. 9, 2008 which claims the benefit of Great Britain Application No. 0718994.7, filed Sep. 28, 2007, the disclosures of which are herein incorporated by reference in their entireties.

FIELD OF THE INVENTION

The present invention relates to the production of phthalic anhydride and in particular to the generation of mixtures of ortho-xylene and an oxygen-containing gas, particularly air, as the reactor feedstock for the production of phthalic anhydride. The invention further relates to the production of phthalate ester and hydrogenated phthalate ester derivatives.

BACKGROUND OF THE INVENTION

Phthalic anhydride is an important intermediate chemical in the chemical industry. One important use is in the production of alkyl phthalates such as di-isononyl or di-isodecyl phthalates which are used as plasticisers typically for polyvinyl chloride. These phthalates may be further hydrogenated to the corresponding di-cyclohexanoates. Phthalic anhydride has been produced on an industrial scale for many years, and has generally been produced by the vapour phase oxidation of ortho-xylene with an oxygen-containing gas such as air by passing a mixture of ortho-xylene and the oxygen-containing gas over an oxidation catalyst.

A typical plant for the production of phthalic anhydride comprises a raw material section, in which a hot mixture of the oxygen-containing gas and ortho-xylene vapour is prepared for feeding to the reactor which typically consists of reactor tubes containing catalyst. The reaction is exothermic and the temperature of the reactor tubes is controlled by a temperature control fluid, such as a molten salt, flowing around the tubes.

After the reaction, the crude phthalic anhydride that has been produced passes to a cooling stage where it is cooled, generally by a gas cooler, and is subsequently passed to optionally a liquid condenser and finally to a switch condenser. Finally the condensed phthalic anhydride is subjected to a purification or finishing step.

The efficiency of a phthalic anhydride plant is measured in terms of the number of grams of ortho-xylene that can be processed for each normal cubic meter of oxygen-containing gas or air that is fed to the raw material section (known as the loading). The greater the amount of ortho-xylene per unit of gas flow, the greater is the efficiency of the facility. Considerable attempts have been made over the years to increase the loading, and loadings above 80 gram/Nm$^3$ of ortho-xylene in air have been reported.

One difficulty in the manufacture of phthalic anhydride is that, at the temperatures required for the reaction of air and ortho-xylene, the mixture becomes flammable and explosive at a loading above 44 gram of ortho-xylene per normal cubic meter of air. Accordingly, great care must be taken to avoid or reduce the likelihood of explosions. When an explosion occurs and the flame velocity exceeds the velocity of sound, this supersonic explosion is called a detonation. Otherwise, at subsonic flame velocities, it is called a deflagration. By the provision of an adequate number of escape ducts, such as chimneys, sealed off by rupture discs, at critical locations, the occurrence of a detonation is avoided, while the burning gas from a deflagration is relieved to a safe location. One or more rupture discs are conveniently located on the ortho-xylene vaporizer, at the reactor inlet and outlet, and on downstream equipment and the sections of the piping operating within the flammability limits. These rupture discs can be of any suitable design although reverse buckling or bending rod type are preferred. One of the areas in a phthalic anhydride facility that is prone to a deflagration is the raw material section where the ortho-xylene and the air are mixed. One of the reasons for a deflagration to occur is if there is incomplete vaporisation of the ortho-xylene or a concentration inhomogeneity in the vapour/air mixture at the time when it reaches the oxidation catalyst. Other reasons can be poor mixing of the heated ortho-xylene and the heated air, discharges from the build-up of static electricity, or the decomposition of peroxides formed from feed impurities like cumene or styrene. Also pyrophoric compounds may be formed and cause a deflagration.

The process therefore requires a mixture of oxygen-containing gas and ortho-xylene that is as homogenous as possible, operating at all points above the dew point of ortho-xylene. Typically liquid ortho-xylene is preheated to about 140° C. under elevated pressure, flow metered with mass flow meters, and forced into a spray nozzle configuration for injection into the heated oxygen-containing gas, which is typically air. The hot liquid ortho-xylene is thus sprayed as a fine mist into the hot oxygen-containing gas where the ortho-xylene is vaporised.

In a typical commercial process, the generation of a feed gas mixture has to date been performed as follows. Process air is sucked in from the surroundings through a filter by means of a blower, and compressed to a pressure level which allows the conveyance of the air stream through the phthalic anhydride plant. This process air stream is heated in a heat exchanger disposed downstream of the blower, and its flow is metered and controlled accurately. Parallel thereto, liquid ortho-xylene from a storage tank is brought to a preliminary pressure by means of a pump and passed through a basket type filter, an accurate flow meter and control device, and routed to a preheater before it is fed to an evaporator, vaporizer drum or spray drum. In the evaporator, the preheated ortho-xylene is injected in liquid form into the heated air stream, parallel to the air flow, by means of a nozzle system. The fine ortho-xylene droplets completely evaporate in the air stream, and a further smoothening of the radial concentration and temperature profiles in the gas stream is achieved by means of a homogenisation stage (a homogenizer section comprising e.g. a static mixer). This homogenised feed gas subsequently enters the reactor, typically a tubular reactor filled with catalyst, where a partial oxidation of ortho-xylene with atmospheric oxygen takes place to form phthalic anhydride. The oxygen is typically present in significant stoichiometric excess.

This process for the generation of feed gas has successfully been used, but with the successive introduction of higher ortho-xylene loads in the air stream (above 80 g of ortho-xylene per Nm$^3$ air) the process has shown potential weaknesses with regard to the explosion safety of the raw material section of the plant. The lower explosion limit of a gaseous mixture of ortho-xylene and air is about 44 g of ortho-xylene per Nm$^3$ of air. It has been found that the minimum energy required for igniting the mixture is greatly decreased with increasing ortho-xylene loading, and therefore the desire to increase the ortho-xylene loading increases the possibility of an explosion. However, to a great extent, the economics of the overall phthalic anhydride production process depends upon increasing the loading of ortho-xylene per Nm$^3$ of oxygen-containing gas or air. It is therefore of basic importance that plants with a loading in the range of 80 g ortho-xylene/Nm³ air to 120 g ortho-xylene/Nm³ air must be operated safely.

U.S. Pat. No. 6,984,289 B2 relates to a process for the production of phthalic anhydride by the oxidation of ortho-xylene with air and with a loading of 80 g to 100 g of ortho-xylene per Nm³ of air. This higher loading is said to be made possible by complete evaporation followed by superheating of the ortho-xylene prior to admixture with air. DE 20 2005 012 725 U1 provides a system in which ortho-xylene is sprayed through nozzles into an air stream in which the flow cross-section of the air feed tube is reduced downstream of the spray nozzles, so that vapour velocity and turbulence are increased, thereby improving the mixing of the reaction components, and in this way the risk of explosion is reduced. DE 20 2005 012 725 U1 also provides a cone-shaped perforated screen at either side of the spray nozzles to divert the pressure wave from an explosion occurring in the evaporation section towards the rupture disks, thereby protecting the equipment upstream and downstream of these screens from damage by a shock wave. These screens assist also in homogenising the flow of air and the flow of the air/ortho-xylene mixture.

DE 10 2004 052 827 A1 is concerned with the preparation of a homogeneous mixture of ortho-xylene and air as a feed for the production of phthalic anhydride. DE 10 2004 052 827 A1 employs a series of arms or lances carrying spray nozzles to inject ortho-xylene into a stream of hot air. DE 10 2004 052 827 A1 further provides a sieve basket comprising concentric cones for directing the flow of air and homogenising the flow profile of the air entering the mixing chamber. In this way catalyst damage due to the carry over of unvaporised droplets of ortho-xylene onto the catalyst is reduced. According to DE 10 2004 052 827 A1 the ortho-xylene can be supplied to the nozzle from a supply line in which the ortho-xylene is held at a temperature above its flash point, typically in the range of 135-140° C.

A problem with the system of DE 10 2004 052 827 A1 is that erosion, particularly by cavitation of the ortho-xylene, can occur within the spray nozzles, which in turn leads to irregular spray patterns of ortho-xylene, perhaps leading to the formation of larger ortho-xylene droplets, and in turn leading to explosive conditions. It is believed that cavitation can be caused by the spontaneous formation of bubbles in the liquid within the spray nozzles which then collapse and in so doing they create shock waves in the liquid which erode and damage the nozzle material surfaces.

US 2003/0013931 also discloses a process and apparatus for the production of a homogeneous mixture of ortho-xylene and air in the production of phthalic anhydride, wherein the ortho-xylene is atomised by means of six axial hollow cone swirl nozzles. US 2003/0013931 is concerned with avoiding upsets in the homogeneity of the o-xylene vapor/air mixture produced by fluctuating operating parameters, The document is not concerned with erosion of the nozzles or the resulting damage to nozzle material surfaces.

Spray nozzles are offered in a wide variety of construction materials, including various polymers. In the chemical process industry, the typical need to resist contact with organic liquids reduces the choice in construction materials to the specialised polymers and metals. Metals are typically preferred because of their typically higher mechanical strength. We have however found that many of the metals of which spray nozzles are made show weaknesses in the production of the mixture of ortho-xylene and oxygen-containing gas, as they are insufficiently resistant to erosion, in particular by cavitation. Many metals are also subject to corrosion under the hot and humid conditions occurring in the vaporiser. Both of these weaknesses may lead to deformation over time of the nozzle surfaces in contact with the liquid ortho-xylene, such that the sprayed mist of ortho-xylene becomes less homogeneous. The droplet size distribution becomes broader and the larger droplets may take more time to evaporate. The droplet density of the mist also becomes less uniform and coalescence may occur in areas of higher droplet density. The lower homogeneity of the mist may therefore lead to an increased risk for deflagrations over time.

A further problem associated with the spray nozzle system is to provide an effective seal where the spray nozzles are connected to the rest of the nozzle system, to prevent leakage of ortho-xylene and the development of larger liquid droplets which, as mentioned earlier, can lead to explosive conditions. It has been suggested to use polytetrafluoroethylene tape to create a seal between the nozzle and the rest of the nozzle system, but this has the disadvantage that the polymeric tape is not electrically conductive and its use can lead to electrostatic build up, increasing the risk of explosion. Furthermore the polytetrafluoroethylene tape may be torn apart particles can be created inside the nozzle which may destroy the flow pattern, leading to the formation of larger droplets of ortho-xylene and the risk of explosions.

It is important that a homogenous mixture of ortho-xylene and oxygen-containing gas is formed for feeding to the reactor and this may be accomplished by enhancing the rate of ortho-xylene vaporisation. Furthermore it is important that the ortho-xylene does not coalesce or condense and form liquid deposits within the raw material section of the plant, to reduce the risk of explosion when liquid deposits are formed. We have found that this may be accomplished by employing a particular nozzle system and a particular set of conditions within the nozzle to spray the ortho-xylene into the hot oxygen-containing gas. In addition, we provide a particular sealing system to prevent the leakage of liquid ortho-xylene. The nozzle system of this invention, including the sealing system, is particularly useful when used in combination with a specially designed oxygen-containing gas feed system and a particular design of oxygen-containing gas and ortho-xylene mixing system.

SUMMARY OF THE INVENTION

The present invention therefore provides a system for mixing ortho-xylene with an oxygen-containing gas, which system comprises an ortho-xylene evaporator vessel fed with a stream of oxygen-containing gas, and provided with a lance projecting into the stream of oxygen-containing gas, which lance is provided with a metal spray nozzle adapted to inject droplets of liquid ortho-xylene into the stream of oxygen-containing gas concurrently with the direction of flow of the stream of oxygen-containing gas, in which the metal at the surface of the spray nozzle, that in use is in contact with the liquid ortho-xylene, has a hardness expressed as a Vickers hardness number of at least 200.

The invention further provides for a process for the production of a gaseous mixture of ortho-xylene and an oxygen-containing gas comprising mixing ortho-xylene and heated oxygen-containing gas employing a system according to the present invention.

In another embodiment, the invention provides for the use of a gaseous mixture of ortho-xylene and an oxygen-containing gas, as produced by a process according to the present invention, as a feed to a reactor containing a catalyst for the production of phthalic anhydride, The advantage is that high loadings of 80-120 grams of ortho-xylene per Nm3 of oxygen-containing gas may be used over long periods of time without process upsets.

The invention further provides for a process for the production of phthalic anhydride comprising producing a gaseous mixture of ortho-xylene and an oxygen-containing gas by the process of the invention, and contacting the mixture with an oxidation catalyst under oxidation conditions to form the desired phthalic anhydride. The production of phthalic anhydride in this process may be performed with high ortho-xylene loadings over extended periods of time such that a high volume efficiency of the process may be continuously achieved.

The hardness of a metallic material is usually measured on the surface of a metal part. When a part is treated such that the surface is harder, on purpose, than the core hardness, the term "surface hardness" may sometimes be used, in order to differentiate from parts that have not been treated, or treated by a "through hardening" treatment to increase the material hardness throughout the part. In this document however, the terms hardness and surface hardness with respect to a construction material or object are used interchangeably.

A widely used method of measuring the hardness of a metallic material is explained in ASTM standard E92 "Standard Test Method for Vickers Hardness of Metallic Materials"—latest version being E92-82 (Reapproved 2004), which expresses the hardness of a metal by a Vickers hardness number (HV).

Various construction metals for spray nozzles, such as the annealed carbon or stainless steels that are very conventional construction materials in the chemical process industry, but also brass, titanium, tantalum and more noble materials, may have Vickers hardness numbers as low as 100-160 or even below. While some of these would be of interest because of their better corrosion resistance, we have found that metals having such low Vickers hardness numbers are less suitable for spray nozzles that need to spray heated liquid ortho-xylene in a stream of hot oxygen-containing gas because the surfaces of those spray nozzles become rapidly damaged. We therefore prefer the metal at the surface in contact with the liquid to have a Vickers hardness number of at least 250, preferably at least 300, more preferably at least 400 or at least 450, even more preferably at least 600.

The desired metal hardness may be achieved by selecting a suitable construction material for the nozzle or by a treating the nozzle after fabrication to increase the hardness of the metal it is constructed of. These hardening treatments can have the purpose to increase the hardness throughout the part and including the core, i.e. "through hardening", or to increase the hardness primarily at or near the surface of the part, i.e. by "surface hardening". Known surface hardening treatments are nitriding (including gas, ion, plasma nitriding as well as Kolsterising®), case-carburizing and borosing.

When steel is used as construction material of the nozzle, we prefer to achieve the desired hardness by using hardened steel. Various techniques for hardening steel are known in the art. One of the techniques is nitriding, and it is believed that the introduction of nitrogen atoms in the steel atomic matrix introduces inter-atomic tensions which greatly improve the hardness of the metal. Many of these techniques are bulk techniques and have a "through" hardening effect, i.e. affecting the metal in high depth, including the core of the metal part. These "through" hardened steels are suitable, but we prefer steel that is "surface hardened", i.e. where the hardening treatment is a surface hardening treatment applied on the nozzle, and which treatment primarily affects the hardness of the metal at the outer surfaces of the spray nozzle. With these surface hardening treatments, Vickers hardness numbers of 700, 800, 900, 1000 or even 1200 and above can be achieved. We have found that the beneficial effect is then more pronounced, and that surface hardened steel spray nozzles perform better than the through hardened alternatives.

We also prefer the metal of the spray nozzle, including the metal at the surface that is in contact with the liquid ortho-xylene, to be corrosion resistant. Corrosion may be caused by the presence of oxygen and/or water coming from various sources such as with the oxygen-containing gas or being formed by oxidation reactions. We prefer to use corrosion resistant steel types, i.e. steel types that exhibit corrosion rates of at most 0.25 mm/year (equivalent to 10 mils or milli-inch per year—MPY) under the process conditions of the vaporiser, preferably corrosion rates of at most 0.20 mm/yr (8 MPY), more preferably at most 0.15 mm/yr (6 MPY), and even more preferably 0.10 mm/yr (4 MPY). Suitable stainless steels have a minimum chromium content of at least 13% wt, but more preferably at least 15% wt or even more preferably at least 17% wt, and the alloy may contain further metals such as nickel, manganese, and/or molybdenum. Suitable types are e.g. the SS 304, 316 or 317 types.

Martensitic or ferritic stainless steels may be used, but we prefer to use austenitic stainless steels, because of their better corrosion resistance. The typical lower hardness of the austenitic stainless steels compared to the other types can be overcome by the hardening treatment, in particular the surface hardening treatment. Our preferred spray nozzle is therefore made of austenitic stainless steel that has been surface hardened, preferably by nitriding, more preferably by cold nitriding such as by Kolsterising®.

In a further embodiment the invention provides a system in which a metal seal is provided between the metal spray nozzle and the metal lance which carries the spray nozzle. The use of a metal gasket as the seal provides a system with good electrical conductivity in which the development of an electrostatic charge in the spray nozzle is reduced by allowing it to dissipate via the lance, and the risk of explosion is accordingly reduced. Preferred metals from which the seal gasket may be made include copper and aluminium, because of their relative softness, improving the seal, and their high electrical conductivity, improving the distribution of any static charge from the nozzle to the nozzle system. Most preferred is a seal gasket made of middle hardness or semi-hard red copper, preferably of the SF-Cu classification according to DIN 1.7670 or an O61 annealed copper according to ASTM B111. The spray nozzles are typically screwed onto threaded stubs sticking out from the lances, or are preferably screwed into internally threaded holes provided in the lances. We prefer that the spray nozzle is provided with a conical surface facing the seal ring. This brings the benefit that the metal seal ring becomes well centred when the spray nozzle is screwed onto the lance. The softer seal ring metal, as compared to the spray nozzle and lance metals, may deform such that the contact surface between the spray nozzle and the seal ring is increased and the seal property is improved. In order to create this deforming effect, we prefer to screw the spray nozzle onto the lance with at least a minimum torque, which in case of the preferred copper seal metal preferably is at least 3 Nm. In addition, the metal seal ring may also be provided with a conical surface matching the surface of the spray nozzle, further increasing the contact surface with the spray nozzle and improving the seal property.

In a further embodiment of the present invention the vaporiser or evaporator vessel preferentially has a circular cross section and the ortho-xylene is supplied to the lances from a single line which feeds a supply ring linked to the nozzles around the circumference of the vaporiser. In this way the pressure at which the ortho-xylene is fed to the spray nozzles can be maintained substantially constant, leading to the production of a similar mixture of air and ortho-xylene by each nozzle.

In a further embodiment the ortho-xylene is supplied to the spray nozzles at a temperature below the vaporisation temperature of ortho-xylene at the pressure inside the vaporiser. The boiling point of ortho-xylene at the typical 0.46-0.49 barg pressure in the vaporiser is about 160° C. Controlling the ortho-xylene feed temperature, after preheating, to below this temperature enables the ortho-xylene to stay as much as possible in the liquid phase inside the lance(s) and in particular inside the spray nozzle. The temperature is preferably only slightly below the vaporisation temperature, for more rapid vaporisation upon spraying, and a temperature in the range 120 to 160° C. is preferred. Within this range, we prefer a temperature in the range of 125 to 155° C., preferably 130 to 150° C., more preferably 132 to 146, even more preferably 135 to 144° C. and particularly 137° C. to 142° C., especially 139 or 140° C. is preferred. Use of this temperature below the vaporisation temperature keeps the ortho-xylene as much as possible in the liquid phase inside the nozzle also when the liquid ortho-xylene is swirled inside the spray nozzle by spray nozzle internals, such that a venturi effect may result which sucks some of the oxygen-containing gas into the nozzle. This leads to a partial mixing of the liquid ortho-xylene with oxygen-containing gas already occurring inside the nozzles, which is then vaporised as it is sprayed out from the nozzle in the selected spray cone as provided by the design of the nozzle. In addition, because the oxygen-containing gas outside the lance(s) is typically hotter than the liquid ortho-xylene on the inside, heat may be transferred to the ortho-xylene by conduction through the lance walls, and this temperature control range allows for the ortho-xylene to pick up heat before it is sprayed without causing cavitation in the spray nozzle. We have found that the use of these conditions further reduces the erosion by cavitation of the spray nozzles and improves the homogeneity of the oxygen-containing gas/ortho-xylene mixture.

In one class of embodiments of the invention, the spray nozzle is characterised by a symmetry axis, typically in the longitudinal direction of the nozzle and usually in the direction of the flow of the liquid. When the spray nozzle creates a cone as the spray pattern, the axis of the spray cone in many instances coincides with the longitudinal symmetry axis of the spray nozzle. In embodiments where the spray nozzle has a longitudinal symmetry axis, the direction of the longitudinal symmetry axis of the spray nozzle should preferably be parallel to the direction of flow of the gas stream. However, to reduce the risk of coalescence of a part of the ortho-xylene droplets, especially when a plurality of spray nozzles is employed, one or more of the spray nozzles can be located at an angle thereto. A pattern may optionally be formed with at least a part of a series of spray nozzles, alternating the nozzles having the parallel direction with those being directed at an angle thereto.

DETAILED DESCRIPTION

Although the invention is workable with only one lance carrying one spray nozzle for injecting the liquid ortho-xylene into the stream of oxygen-containing gas, we prefer a plurality of lances, and/or preferably a plurality of spray nozzles, to be present, thereby forming a spray nozzle system. The invention includes that the features of the invention are present in at least one of the elements of these pluralities, but preferably in most and more preferably in all of the elements.

In a preferred embodiment of the invention, the evaporator vessel of the mixing system is of substantially circular cross section perpendicular to the direction of the gas flow, and a plurality of lances are provided around the circumference of the evaporator vessel, extending across the cross section of the vessel.

In yet a further preference, eight such lances are projected into the evaporator vessel from the circumference of the vessel.

Preferably, when a plurality of lances is provided, the lances are positioned equidistant from each other around the circumference of the vessel.

In another preference, a lance consists of two limbs of different length, thus extending a different distance across the cross section of the vessel.

A lance is preferably provided with a plurality of spray nozzles.

The spray nozzle, or one or more of the plurality of spray nozzles, may be inclined at an angle of from 0° to 45° to the direction of flow of the stream of oxygen-containing gas, and, when inclined, preferably alternate nozzles are inclined relative to each other.

The number of nozzles that are employed depends upon the capacity of the phthalic anhydride facility and the diameter of the vaporiser or evaporator unit or vessel.

It is preferred that, when the nozzles are facing sideward, adjacent nozzles are inclined at different sides of the longitudinal axis of the lance(s), forming an alternating pattern, thereby avoiding that the spray from one nozzle interrupts the spray pattern from an adjacent nozzle.

In a further preferred embodiment of a two-limb lance, the longer limb of the lance is provided with ten nozzles and the shorter limb is provided with six nozzles.

In another further preference, the nozzle closest to the wall of the vessel is positioned at least 130 mm from the wall of the vessel, to avoid the spray cone from the nozzle hitting the vessel wall. It has been found that, if nozzles are positioned at a distance of less than 100 mm distance from the wall, wet spots can occur on the vessel wall.

The lance carrying the spray nozzle(s) is hollow for the delivery of the liquid ortho-xylene to the nozzle(s), and the end of (each limb of) the lance(s) is preferably capped so that ortho-xylene cannot flow out of the end of the lance.

The design of the spray nozzle itself is also important, and we prefer to use a nozzle having a 60-70° spray cone. A vaporising nozzle supplied by Schlick-Dusen hollow-cone type 121V with a 1.3 mm bore diameter is particularly useful.

As discussed before, the spray nozzles are preferably made of hardened stainless steel, to minimise wear and corrosion in order to maintain integrity of the desired spray cone over extended plant runs. Preferably austenitic stainless steel is used for making the nozzles because of the better corrosion resistance.

The spray nozzles can be damaged by dirt and particles and by any surface treatment, and the resulting damage, in particular of the relatively softer austenitic stainless steel nozzles, is reduced by manufacturing the nozzles from hardened stainless steel. This is conveniently achieved by surface hardening of the steel spray nozzle. The invention therefore provides for a mixing system wherein the spray nozzle is made of surface hardened steel.

The surface hardening may conveniently be accomplished by nitriding, preferably by cold temperature nitriding to maintain dimensional stability, and more preferably by Kolsterising®. The invention therefore provides for a mixing system wherein the spray nozzle is hardened by nitriding the surface of the spray nozzle.

Slight surface defects in the nozzle may cause cavitation and erosion, and we have found that the two major causes of nozzle damage are particles and superheated ortho-xylene. The particles come from ortho-xylene feed (rust, sand, glass or mineral wool or fibre, typically from a tank floating roof seal that erodes) and hence it is important that the ortho-xylene feed be filtered. It has been found that a 20 micron, basket type filter did not keep all particles out, and it is therefore preferred to use, optionally in addition, a 10 micron size cartridge filter, more preferably a 5 micron size, most preferably a 1 micron size cartridge filter downstream thereof.

In a preferred embodiment, the invention provides for a system whereby the ortho-xylene is filtered through a filter adapted for filtering particles no larger than 5 microns prior to introduction into the lance(s).

It is also important to prevent fouling of the nozzle with unwanted material which can come from the upstream equipment and valves, and we prefer to use metal seals, particularly copper seals, to avoid the problem when using Teflon seals, since the Teflon can be softened by the hot ortho-xylene so that Teflon fibres are formed which can plug and/or damage the spray nozzles. We also have observed that, when applying polymer tapes such as polytetrafluorethylene like Teflon, these tapes can get damaged by the mechanical forces required for mounting the spray nozzle into the lance. Fragments of damaged tape frequently ended up at the interior of the spray nozzle.

It is preferred that the liquid ortho-xylene to the spray nozzles is fed from a common source, so that the ortho-xylene is injected under equal pressure from all the nozzles. In this way each nozzle can produce a similar mist of ortho-xylene within the hot oxygen-containing gas stream and the mist can have a substantially uniform ortho-xylene droplet size. In a preferred embodiment ortho-xylene is sprayed through a nozzle system to yield a droplet mass-distribution of from 5 to 15%, typically 10%, of particles that have a diameter not larger than 40 micron, preferably not larger than 35 or not larger than 30 micron, more preferably not larger than 25 or even not larger than 20 micron, from 30 to 70%, typically 50% of particles that have a larger diameter but not larger than 75 micron, preferably not larger than 65 micron, more preferably not larger than 55 or even not larger than 50 micron, from 20 to 40%, typically 30%, of particles having a yet larger diameter but not larger than 110 micron, preferably not larger than 95 micron, more preferably not larger than 75 micron, and the balance from 0 to 15%, typically 10%, of particles having a even yet larger diameter but preferably not larger than 200 micron. We have found that this may be accomplished if the ortho-xylene is sprayed with a differential pressure of at least 5 bar, preferably at least 7 bar, more preferably at least 9 bar and most preferably at least 10 bar, especially 12 bar, through a spraying nozzle having a bore diameter of at most 3 mm, preferably at most 2.5 mm, even more preferably at most 1.5 mm, and most preferably at most 1.3 mm.

In a further preferred embodiment, the liquid ortho-xylene is fed from a common source. As one alternative of such embodiment, a ring system may be provided for the feed of liquid ortho-xylene to the lances that carry the nozzles. Care should be taken to maintain the ring system and the nozzle system at the desired temperature which may be accomplished by highly effective thermal insulation of the external surface of the piping and other metal parts that compose the ring system and the spray nozzle system, as well as of the piping through which the preheated air flow is guided.

In a preferred embodiment of the invention, at least part of the external surface of the ring system and/or the spray nozzle system therefore is thermally insulated.

It is also important that there are no leaks of hot liquid into the heated gas flow at undesired locations, such as where the nozzles are attached to the lance. Therefore we prefer to have an effective seal between the spray nozzles and the lances which carry the nozzles, and we have found that a heat treated copper gasket, preferably of O61 annealed copper according to the ASTM B111 standard, positioned where the spray nozzle connects with the lances, provides an effective seal. This seal material also provides excellent electrical connection between each nozzle and the respective lance.

The oxygen-containing gas is usually air and is typically ambient air, which is filtered to remove dust, and particularly sea salt because that may poison the oxidation catalyst. The gas is typically preheated, preferably to 180-210° C., usually in two stages. Higher temperatures are required for higher ortho-xylene loadings, to ensure a high mixture temperature. At the higher ortho-xylene loadings of at least 80 g/Nm$^3$ in air, it is our preference to operate with a reactor inlet temperature of 168-172° C., after passing the homogenizer section, to ensure the completeness of the vaporisation. Preferably after preheating and before the mixing, the hot gas passes through turbulence reducers ("quieting" vanes) and its flow rate is preferably then measured, e.g. by means of a venturi device, so that it may be accurately controlled, such as at about 4 Nm$^3$/h/tube relative to the number of reactor tubes, which is our preferred flow rate.

We have found that reducing the turbulence in the hot gas makes it much easier to have an accurate and representative measurement of the gas velocity, e.g. by means of a simple and low pressure drop device as a venturi device, and thus of the gas flow. These "quieting" or "straightening" vanes can be of any suitable type or form to obtain the turbulence reducing effect. We prefer, because of the simplicity of design and construction, to fill the typically large diameter pipe duct for the hot gas, such as e.g. a 48 inch or 122 cm nominal diameter pipe, over a length of at least 1.5 or 2 meter or about 1-2 pipe diameters, as much as possible with preferably thin-walled pipes of a significantly smaller diameter, such as 3 inch (about 8 cm) or 4 inch (about 10 cm) pipes, and preferably using a combination of different diameters to obtain a better filling of the large pipe duct. The better the large diameter pipe duct is filled, the lesser gas can bypass along the perimeter of the vanes and the better the overall quieting effect. Many construction materials can be selected for fabricating these straightening vanes, but we prefer steel, typically carbon steel, because the steel pipes can be welded to each other and the total system can then obtain sufficient structural integrity. We have found that any welding, soldering, brazing or glue applying operation to connect such vanes to each other and/or to the larger pipe duct needs to be performed carefully and with sufficient aftercare and cleaning, because we have found that debris from the connecting operation, such as slag from welding, which may remain in the assembly upon commissioning, can be carried with the gas downstream and disturb operations integrity of the downstream evaporator, the homogeniser and/or even at the reactor inlet. When welding is used, we prefer to use longitudinal welds rather than spot welding because of this reason.

The hot gas may then, typically after the flow measurement, enter the evaporator through the bottom sieve basket protecting the upstream equipment from any shock wave coming from downstream. The ortho-xylene is preferentially filtered, preferably to 1 micron, advantageously preheated to 135-145° C., and sprayed into the hot gas through the nozzle system of the invention as a fine mist cloud, so that the ortho-xylene vaporises in the hot gas. As mentioned previously it is our preference to limit the ortho-xylene preheating temperature to avoid ortho-xylene superheating and flash vaporisation, because we have found that this can lead to cavitation inside the spray nozzle, leading to nozzle damage. The ortho-xylene concentration in the air is typically between 32 and 120 gram/Nm$^3$ and the reactor may be started for example with a loading of 32 gram/Nm$^3$ and the loading may be gradually increased further to a concentration range of 80-120 grams/Nm$^3$, preferably 90-105 gram/Nm$^3$. After passing through the upper sieve basket protecting downstream equipment from shock waves originating in the evaporator, the ortho-xylene vapour/gas mixture preferably passes to the reactor inlet through a homogenizer, consisting of a perforated screen and a static mixer. It is preferred that the static mixer comprises two stages, in one of which the ortho-xylene gas mixture passes both from top to bottom and from bottom to top in the vertical plane within the mixer, and in the other section it passes from side to side in the horizontal plane within the mixer. It is further preferred that the side to side section is the second section through which the ortho-xylene gas mixture passes.

The ortho-xylene, as vapour but particularly as liquid, has the tendency to accumulate an electrostatic charge when experiencing shear or turbulence, e.g. when being pumped or by passing restrictions, such as filters and spray nozzles, due to its very low conductivity, which is typically in the order of 0.1 picoSiemens per meter for the liquid phase. The Siemens or Mho is the reciprocal of the Ohm, the unit of electrical resistance. Such a low electrical conductivity implies that ortho-xylene has a high resistance for electrostatic charge relaxation. It is therefore preferred to provide ample residence time in the ortho-xylene preheater of the vaporiser feed system, to allow for electrostatic charge relaxation. It is also preferred to provide adequate grounding to earth of all piping, instrumentation and equipment in the whole phthalic anhydride manufacturing plant and more specifically in those areas that are in contact with ortho-xylene liquid and/or vapour. It is even more preferred to minimize or to eliminate electrostatic potential differences between connecting flanges of equipment, piping and instrumentation by providing at least one high conductivity metal wire or cable strongly and electrically well attached to both of the these flanges or pieces of equipment, and this most preferably at every equipment connection. For such a connection, we prefer that a metal plate can be welded to the flange, that the wire or cable is connected to a metal clamp, and that the clamp is bolted to the metal plate to allow for minimum electrical resistance. We also found that the cable should preferably be as straight and short as possible, without any loops. It is most preferred to have these connections on every part of the ortho-xylene vaporiser, the external parts but even more importantly also the internal parts, as the hold up volume is typically very limited, and this helps to allow for sufficient electrostatic charge dissipation from the ortho-xylene mist after this has left the spray nozzles, because these spray nozzles contribute to charge build up in the ortho-xylene mist and such charges may further concentrate in the liquid droplets as the liquid continues to vaporise and the droplets become smaller. A further preference is not to have a thermowell in the vaporiser and homogenizer system where ortho-xylene mist is present, because the thermowell can act as an antenna for building up an electrostatic charge.

It is also important to maintain the mixture flowing from the mixing zone towards the reactor in a homogeneous form. In a preferred embodiment the stream passes through an alternating mixing device, to which initially the mixture passes through a vertical (up and down) mixing device and subsequently passes through a horizontal side to side mixing device. Irrespective of the technique that is used, it is important that a homogenous mixture of ortho-xylene and oxygen-containing gas (air) is maintained from the injection zone up to the catalyst bed in the reactor.

The ortho-xylene vapour/gas mixture produced by the techniques of this invention then enters a multi-tubular reactor filled with coated ceramic ring catalyst particles for reaction at a temperature typically of from 350 and 460° C. The inlet pressure of the reactor tubes may be in the range of 0.3 to 0.6 barg, typically about 0.45 barg, and the pressure drop across the tubes may be in the range 0.2-0.4 bar, typically about 0.3 bar. We prefer to use a catalyst giving a lower pressure drop across the tube, because this allows to reduce the discharge pressure, and consequently also the energy requirement, of the compressor feeding the oxygen-containing gas to the process, which is an important energy consumer. When replacing a catalyst system having a higher pressure drop with a catalyst system having a lower pressure drop, we found it advantageous to also adapt the air compressor rotor, and if desired also the gearbox and/or its driver, to the new requirements, such that the new operating point remains in the highest efficiency operating envelope of the equipment, and the energy savings could be fully realised. The residence time within the catalyst tubes may be in the range of 0.5 to 2 seconds, typically about 1 second. The tubes are usually arranged vertically, with the reaction mixture of gas and ortho-xylene passing in a downward direction through the tubes.

The oxidation reactor typically is a tubular reactor comprising a plurality, preferably a multitude of tubes, packed with the oxidation catalyst. The tubes are typically arranged vertically. The catalyst beds in the reactor tubes are preceded by a layer of inert rings, preferably uncoated ceramic rings, with preferably a layer thickness of 5-20 cm, which typically is provided on top of the catalyst. The layer of inert rings can be heated from the outside of the reactor tube and the rings are preferably made of a material having a high thermal conductivity, to enhance the heat up of the air ortho-xylene mixture by thermal conduction from the wall of the reactor vessel. A thicker inert layer is less preferred, as it will be at the expense of effective conversion capacity. The inert layer can also provide protection against non-vaporized ortho-xylene droplets and can enable additional mixing of the ortho-xylene/gas mixture. Preference is given to only pack inert material into the upper section of the multi-tubular reactor, at the height of the tubesheet, as it is difficult to remove the heat of reaction if a catalyst were to be present in that location. The preferred catalyst is a multi-layer catalyst system, comprising preferably 3, 4 or even 5 layers, composed of a mixture of vanadium pentoxide, titanium dioxide, and several other metal, alkali and earth-alkali components in varying concentrations, typically coated on a ceramic ring or hollow cylinder material. Such a hollow cylinder may e.g. have 7 mm as the outer diameter (OD) and 4 mm as the inner diameter (ID), and have a height (H) of 7 mm. Alternatively, the cylinder may have 8×6×5 mm as (OD×H×ID) dimensions. The catalyst layers preferably have increasing activity in the direction of flow of the ortho-xylene, oxygen-containing gas mixture. Catalysts which can be used are described, for example, in DE 25 10 994, DE 25 47 624, DE 29 14 683, DE 25 46 267, DE 40 13 051, WO 98/37965 and WO 98/37967. Coated catalysts in which the catalytically active composition is applied in the form of a shell or coating to the support, such as for example in DE 16 42 938 A, DE 17 69 998 and WO 98/37967, have been found to be particularly useful. The catalyst may be pre-calcined or may be calcined in situ in the oxidation reactor, although it is preferred that a pre-calcined catalyst is used, as the use of in situ calcined catalyst is much more sensitive for developing a runaway reaction than a pre-calcined catalyst. A runaway reaction is the result of a rapid increase of the ortho-xylene concentration, for instance from an inhomogeneous ortho-xylene/air mixture. The runaway reaction leads to the formation of a localized hot spot inside the catalyst tube, which can ignite the reacting mixture and also the upstream ortho-xylene/oxygen-containing gas mixture by backfire. In such an event, the flame moves countercurrently against the gas flow direction and at a velocity that is higher than the gas flow velocity.

The tubes in the reactor are preferably thin walled tubes, preferably made from mild carbon steel, and are typically of internal diameter from 20 to 30 millimeters, preferably from 23 to 27 millimeters. It is preferred that the tubes are longer than 2.5 meters, and a length of 3.25 to 4 meters is preferred, more preferably 3.4 to 3.8 meters. It has been found that the use of tubes of this length allows more catalyst to be available to the mixture of ortho-xylene and the oxygen-containing gas, allowing a lower temperature to be used, whilst retaining the conversion which is virtually 100%. The use of the lower temperature results in a higher reaction selectivity to ortho-xylene, which is typically in the range of 80 to 85%. The reaction is highly exothermic and the temperature of the reaction is controlled by providing a coolant flowing around the outside of the tubes within the reactor, on the shell side. The preferred coolant is molten salt, generally maintained at a temperature in the range of from 320° C. to 380° C. The coolant temperature may be increased over the length of a commercial run to compensate for any deactivation of the catalyst. Optionally more than one coolant system may be provided, forming more than one reaction zone in which the temperature may be controlled independently from the other zone(s).

The reactor product is a gas which leaves the reactor usually at about the cooling salt temperature of typically 320-380° C. and typically first enters a gas cooler where it is first cooled, for example to about 175° C. at which temperature the reactor product is still a vapour. The gas cooling may optionally be performed in stages, in between which a finishing reactor may be provided, typically an adiabatic bed of even more active catalyst, to convert any ortho-xylene left over after the first (tubular) reactor. In the next phase of the cooling stage, the gas is optionally cooled further in a liquid condenser, preferably to about 138-142° C. Part of the crude phthalic anhydride is condensed and preferably also separated off, whereas the remaining gaseous material flows to one or more switch condensers. The cooling is typically performed against raising steam from condensate on the utilities side of the cooler and the liquid condenser. We have found that in order to avoid local condensation, and consequently fouling, in the gas cooler, it is preferable to feed a condensate for steam generation that is already at a temperature of at least 135° C., more preferably at least 150° C., if needed by a preheater on this condensate stream. If the phthalic anhydride facility is in the proximity of a phthalate ester production facility, the condensate from the steam used for heating the phthalate ester facility may readily be used for generating the steam in the phthalic anhydride facility, optionally after flashing the condensate to a lower pressure level. The low pressure steam vent from this flashing may also be recovered by condensation to further condensate. The steam generated by the phthalic anhydride facility may be integrated with a steam system supplying other heat consumers.

In a switch condenser, the gaseous phthalic anhydride is desublimated, typically in the form of needles, on a cold surface, a process step that is typically followed by a melting stage. The cooling for the desublimation is preferably performed at about 60° C., typically using a heat transfer oil as the coolant, whereas the melting is preferably performed with a heat transfer oil at about 180° C., typically also with the same type of oil. The switching of the equipment from desublimation to melting and back causes thermal stress and fatigue, in particular on the welds, and we have found that the switch condenser life time may be extended by limiting the temperature change rate of the heat transfer oil to at most 50° C. per minute, and preferably also by limiting the maximum heat transfer oil temperature to at most 180° C.

We have also found that acoustic emission monitoring may be a suitable tool to monitor the development of micro fractures in the steel of the switch condensers, more particularly in the welds therein, and to provide an indication of when these micro fractures may be growing or condensing and eventually lead up to a size where a leak is likely to occur. When a leak occurs, hot oil typically leaks into the product phthalic anhydride and contaminates the product to a typically unacceptable degree, such that the leaking switch condenser must be taken out of service and repaired. We have found that acoustic emission monitoring of the switch condensers may help in forecasting failure risk, in the planning of further inspections and maintenance interventions, thereby introducing a preventive element into the switch condenser maintenance which otherwise would be more strictly remediating.

The products from the liquid condenser and the switch condensers are preferably combined as crude phthalic anhydride, which flows to the intermediate tank for feeding to distillation. The condenser system also purifies the product, the liquid condenser typically reaching 95-98% purity while the switch condensers usually give an even higher purity.

The waste gas of the switch condensers typically has a temperature of 65° C. to 75° C. and can conveniently be disposed of in a catalytic incinerator. The remaining organics in the waste gas may in such a device be combusted at for example 290-350° C. over a multi-layer honeycomb catalyst. The off-gas of the incinerator is then preferably discharged to the atmosphere. Alternatively, the waste gas of the switch condensers can be disposed of into a thermal incinerator or an aqueous scrubber system to recover some of the organic materials from the waste gas, such as maleic anhydride.

After the condensation section, the condensed and desublimated liquid phthalic anhydride passes to a final purification step, composed of a thermal treatment step followed by distillation, typically in one to three stages. The thermal treatment dehydrates any phthalic acid that may have been formed during the oxidation reaction, or downstream thereof under presence of even traces of water, and is followed by or combined with a treatment with a base, which can neutralise any acid species, including remaining traces of phthalic acid, that may be present. The purification may be performed separately on the products from the liquid condensers and the switch condensers or the materials may be combined prior to purification. The dehydration is typically performed by heating, typically to a temperature in the range 250° C. to 290° C., and the neutralisation may be performed with a base such as potassium hydroxide or sodium carbonate. Sodium hydroxide may also be used, but is less preferred because of the risk of stress corrosion. These steps may be performed concurrently in a single vessel or sequentially in two vessels. We prefer however to first heat treat, to dehydrate any phthalic acid present, and then to treat with the base to neutralise, as this optimises the yield of phthalic anhydride (PAN) and avoids the base converting phthalic acid to the undesirable impurity benzoic acid. We also prefer that the neutralisation be performed with potassium hydroxide.

Finally, after the thermal treatment stage, the pure phthalic anhydride can pass to a stabiliser section to remove light components like benzoic acid, followed by a product distillation section to separate the phthalic anhydride product from heavier boiling byproducts, which two sections can be combined in a single section, optionally followed by a heavy by-product concentration section. The phthalic anhydride may then be provided as an intermediate for subsequent reactions either as a melt or as flakes.

Temperature control of the feed mixture and of the oxidation reactor is extremely important, and steam tracing and insulation are preferably employed to prevent condensation of ortho-xylene and reaction products on cold spots. The insulation should be carefully sealed to prevent water entering the insulation, which may impair its performance. It is our preference to provide steam having a pressure of at least 8 barg, more preferably at least 12 barg, even more preferably at least 15 or 16 barg, most preferably as high as 20 barg to the steam tracing provided to the equipment nozzles connecting amongst others the rupture discs which relieve the reactor contents to the atmosphere upon a deflagration. A further preference is to put an insulating mineral wool blanket on top of the rupture disc surface and a poly-urethane foam cap on top of the rupture disc relief stack, to prevent rain and cold air coming into contact with the rupture disc surface and thus preventing any cooling down of the process, even locally. We prefer to use a foam cap instead of a solid plastic cap, such as rigid polyethylene. The foam cap protects against ingress of water, hail or snow into the relief stack and collecting on top of the rupture disc, and creating possible cold spots on the rupture disc. The cap is preferably lightweight and disintegrates easily upon blowing the disc and the resulting foam fragments are dispersed without being a danger to people who may be present in the proximity at the moment of a deflagration. The preferably 3-8 cm thick blanket is laid down carefully onto the disc, such as not to hamper the relieving performance of the rupture disc.

At start-up, it is preferred to operate at a low loading, below the explosive region, for an initial period. For example, the facility may operate for 6-24 hrs at 42 g ortho-xylene loading (below the explosive region) to "burn out" any pyrophoric compounds that may be present inside the process equipment. Pyrophoric compounds may for instance be formed from the reaction products resulting from the corrosive action by acids such as maleic acid and phthalic acid. These include iron maleate, iron phthalate, nickel maleate, nickel phthalate, chromium maleate, chromium phthalate and other organic salts of metals present in the steel of the facility where this is in contact with the ortho-xylene feed and/or with reaction products.

Impurities that may occur in the ortho-xylene feed include cumene or isopropyl benzene, styrene, ethyl benzene and methyl ethyl benzene. It is particularly important for operations at high loading that the cumene level is limited to below 0.3 wt % because at higher cumene levels, in combination with ortho-xylene loadings at and above 85 g/Nm$^3$, the likelihood of having a deflagration increases significantly. It is important to maintain low levels of impurities in the ortho-xylene feed. Peroxides may come from the ortho-xylene. For instance, cumene and oxygen can make hydroperoxide, and this may already occur in the feed tank if that is not blanketed. It may also occur in a truck or a ship during transport of the ortho-xylene. This hydroperoxide is unstable under the vaporising conditions, and can cause a chain reaction forming more cumene peroxide and ortho-xylene hydroperoxide, potentially leading to deflagrations. Styrene, ethyl benzene and methyl-ethyl benzene are other possible sources of peroxides which may develop in the ortho-xylene storage tank or during shipment. We have found that concentrations of styrene exceeding 500 ppm wt may cause polymerisation, and lay down of the resulting polymer on the spray nozzle assembly, which due to its electrical insulating properties eventually leads to build up of electrostatic charge, which may result in a deflagration. Furthermore ortho-xylene and oxygen-containing gas may react to form some ortho-xylene hydroperoxide as an intermediate in the formation of the aldehyde. General fouling may also provide a surface for peroxide formation, and this can occur with improper air filtration, and/or in a dusty environment. Accumulation of peroxide in a layer of fouling is known to initiate deflagrations.

The present invention therefore provides an improved mixing of the hot oxygen-containing gas and the hot ortho-xylene and thus enables operation at high loading whilst minimising the risk of explosion while operating within the explosive temperature range.

BRIEF DESCRIPTION OF THE DRAWINGS

The present invention is illustrated by reference to the accompanying drawings.

FIG. 1 is a schematic illustration of the oxidation section of a plant for the manufacture of phthalic anhydride from a mixture of air and ortho-xylene.

Figure 1:
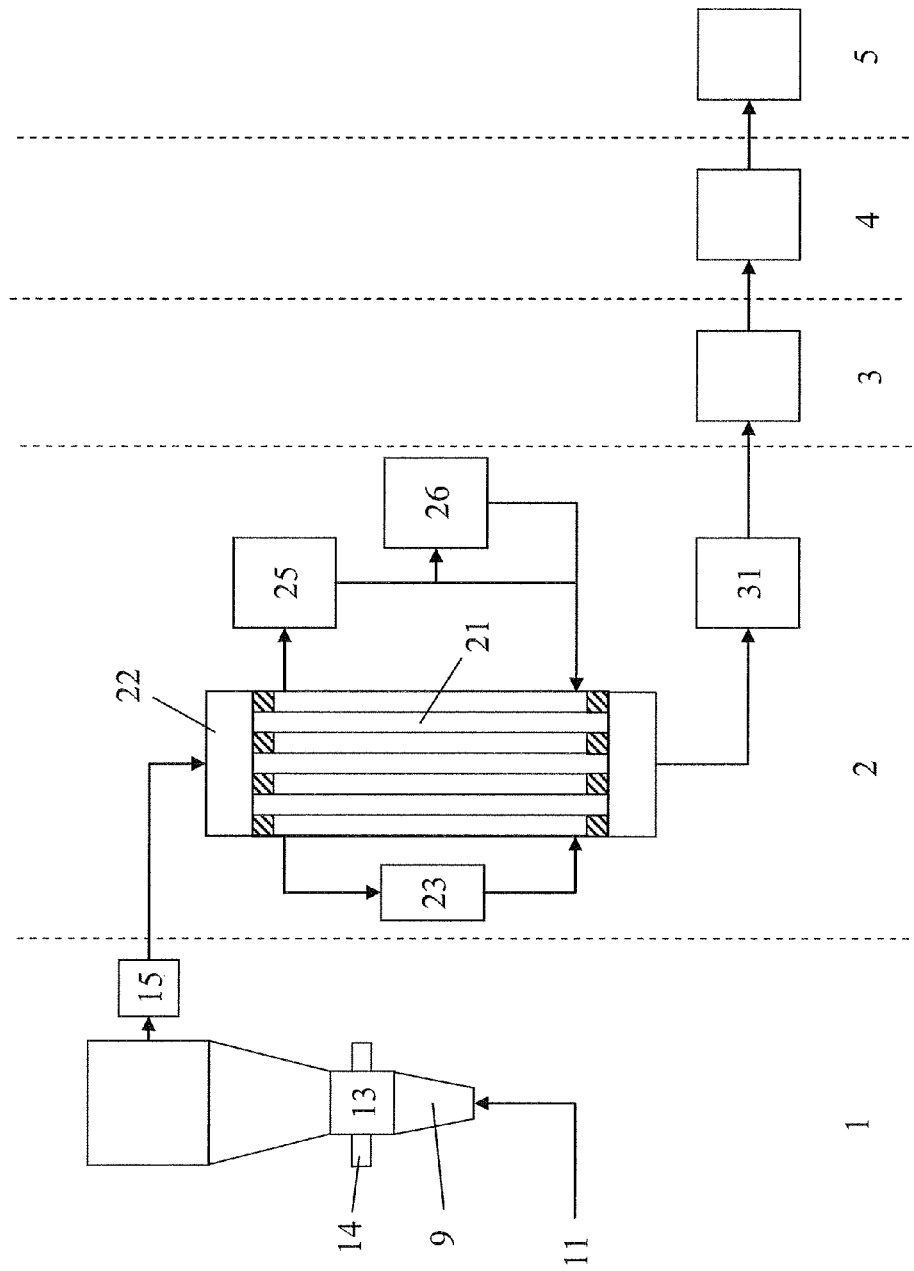
FIG. 1 shows the overall layout of the oxidation section of a phthalic anhydride manufacturing facility.

The oxidation section consists in general of the following sub-sections, the ortho-xylene evaporator section (1); the reactor section (2); the post-reactor section (3); the partial liquid condenser section (4) and the switch condenser section (5).

In the ortho-xylene evaporator sub-section (1) heated air, after passing a first straightening vane system and subsequent accurate flow measurement (not shown), is fed in a pipe (11) through a sieve basket with a turbulence quietening vane system (9) to a zone (13) where it is mixed with a mist of heated ortho-xylene provided from a ring feed system (14); the lances for the introduction of the ortho-xylene are not shown in FIG. 1. The mixture of ortho-xylene and air then passes through the upper sieve basket (not shown in FIG. 1) into a two-stage mixing zone (15) of the evaporator where the mixture is homogenised. The mixture first passes through a perforated screen and then a static mixing device. A preferred mixing device is a Sulzer SMV static mixer with two mixing elements in which the ortho-xylene/air mixture in the first element is mixed in the vertical upward and downward direction followed by mixing in the second element in the horizontal directions.

The mixture then passes to the reaction sub-section (2). The reaction sub-section comprises a reactor (22) containing a series of vertical tubes (21) packed with catalyst (not shown). The internal temperature of the reactor and the temperature of the reaction tubes (21) are controlled by molten salt circulating on the reactor shell side, and which is provided from a salt pump (25). A major part of the salt flows to the reaction tubes for cooling. Part of the salt is passed to a salt bath cooler (26) in which the salt exchanges heat with hot water to generate steam. The returning cooled salt is mixed with the returning salt from the reactor before entering the salt pump. A minor part of the salt is passed to a steam superheater (23).

On exiting the reactor, the phthalic anhydride vapour is cooled in the gas cooler (31) and passes to the optional post-reactor section (3), which may comprise an extra catalyst bed, preferably adiabatic, of even more active catalyst. Next the cooled gas passes optionally to the liquid condenser section (4) where the crude phthalic anhydride is partially condensed, the remaining vapour passing to the switch condenser section (5).

Figure 2:
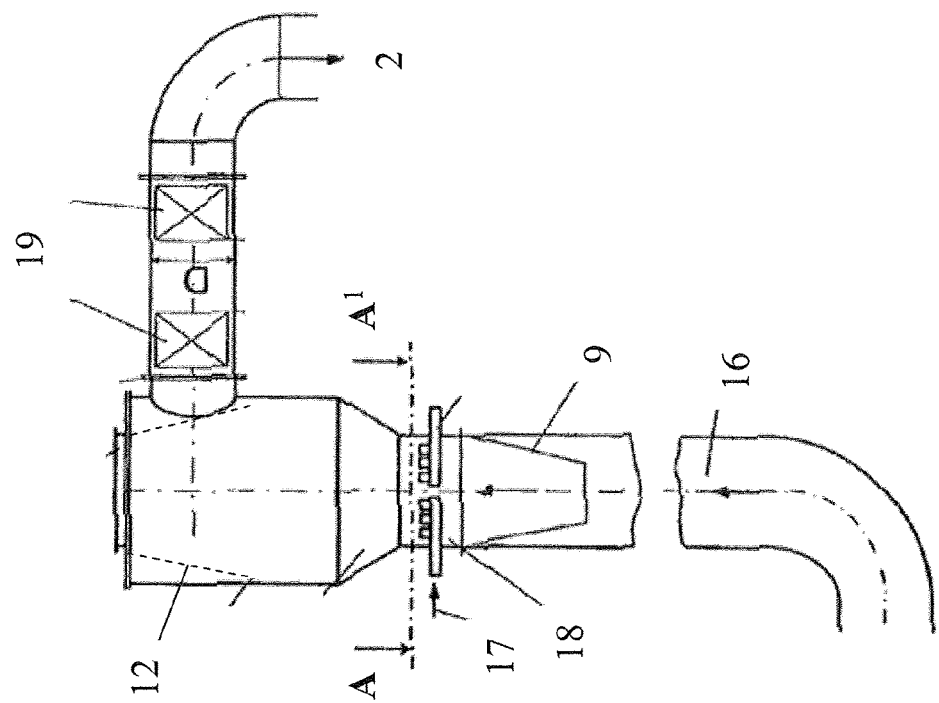
FIG. 2 is a cross-section through the evaporation section of the facility shown in FIG. 1.

FIG. 2 is a schematic cross-sectional illustration of the apparatus in the evaporator sub-section of the oxidation section, as illustrated in FIG. 1. FIG. 2 shows the air stream (16) passing upwards through a lower sieve basket and the quietening vane system (9) and then shows the hot ortho-xylene (17) being injected into the heated air stream through the spray nozzles (18). The ortho-xylene is vaporised in the heated air and the hot vapour mixture passes side-wards through an upper sieve basket (12), which is a perforated screen, and a vapour homogeniser such as a static mixing device (19) before passing to the reaction sub-section (2).

Figure 3:
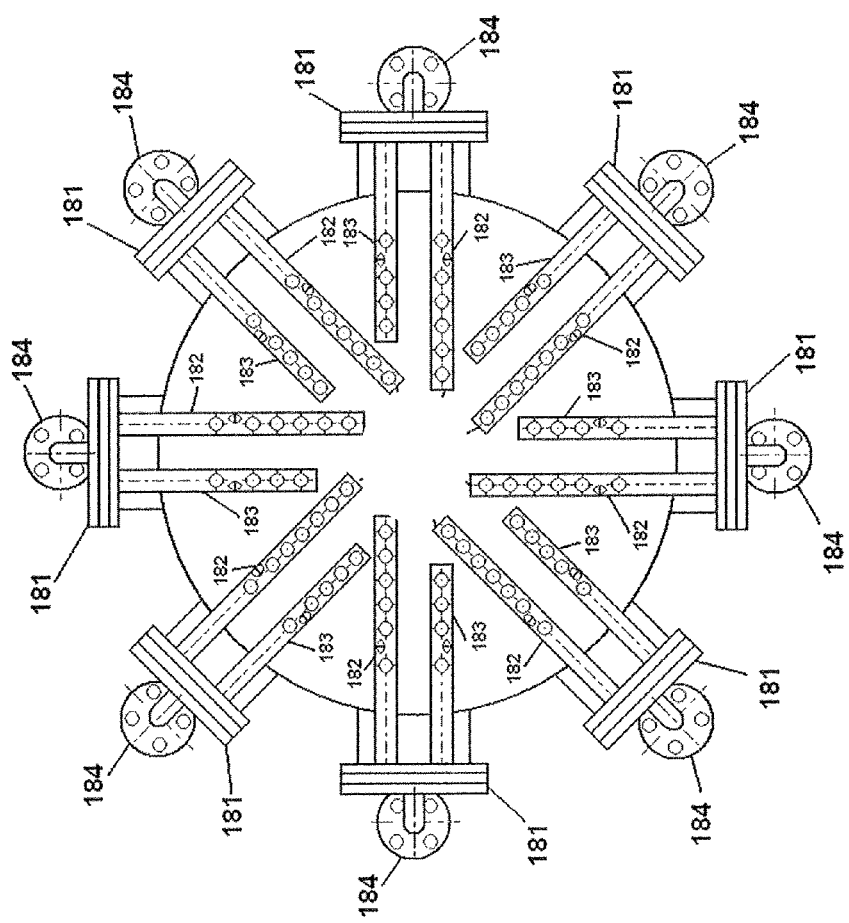
FIG. 3 shows the location of the lances carrying the spray nozzles of the present invention within the evaporator section shown in FIG. 2.

FIG. 3 is a cross section through A-A$^1$ of FIG. 2 looking downwards onto a spray nozzle system (18) that may be employed according to the present invention.

FIG. 3 shows eight lances (181) projecting through the wall of the evaporator radially into the vessel. Each lance is provided with two limbs, a larger limb (182) and a shorter limb (183). Each lance (181) is also provided with means (184) for connection to the supply of heated ortho-xylene. The limbs of the lances are provided with nozzles for the spray of the ortho-xylene into the stream of hot air, shown in one of the possible nozzle arrangements of this invention. In the embodiment illustrated in FIG. 3 the longer limb of each lance is provided with 7 spray nozzles and the shorter limb is provided with 5 spray nozzles, although the number of nozzles can be varied. The connection of the lances to the ortho-xylene supply system is by a ring system (not shown) common to all the lances and the whole introduction system is thermally insulated to prevent cooldown of the ortho-xylene feed.

Figure 4:
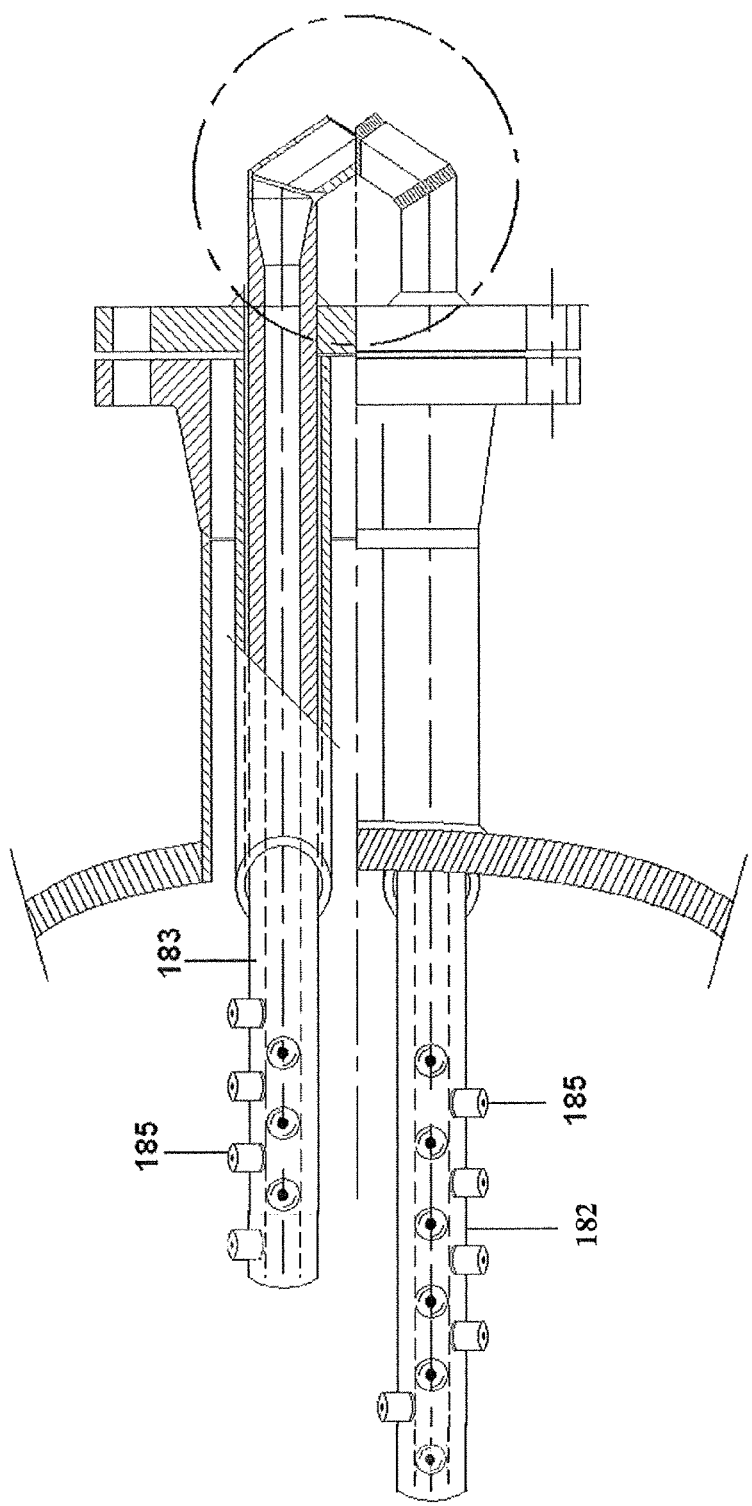
FIGS. 4, 5 and 6 show a single lance and the detail of the distribution and direction of the spray nozzles along the limbs of the lance.
Figure 5:
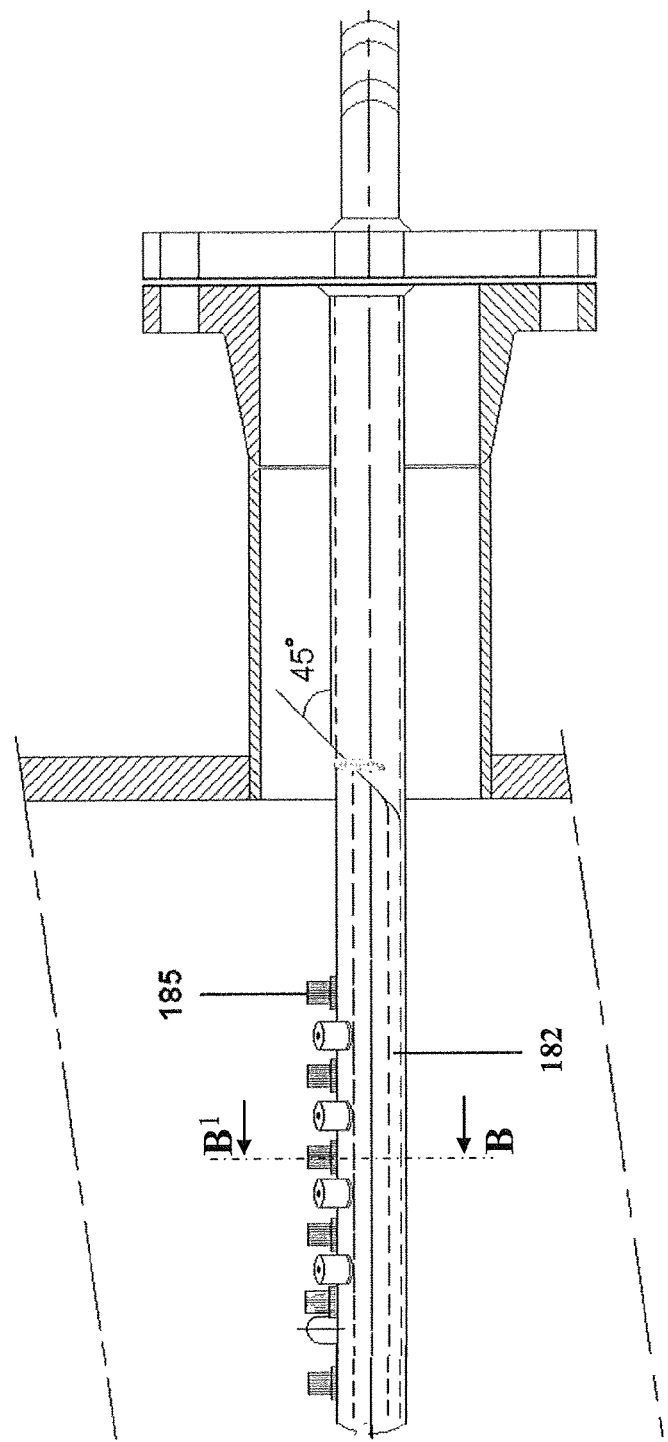
Figure 6:
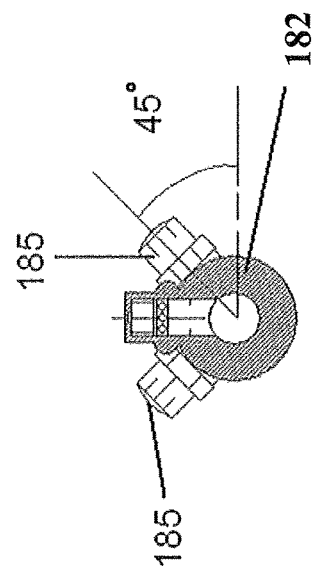

FIG. 4 is a top view of a single lance of a nozzle system of the type shown in FIG. 3, except that in this instance the longer limb of the lance (182) carries 11 nozzles (185) and the shorter limb (183) carries 7 nozzles. The nozzles in FIG. 4 are mounted on the limb of the lance, to spray the ortho-xylene into the air stream, in a specific alternating pattern with the centre axis of the spray cones parallel to and at an angle to the axis of flow of the air stream. FIG. 5 is a side view further illustrating the distribution of the nozzles (185) along a limb (182) of the lance and FIG. 6 is a view of the cross section B-B$^1$ in FIG. 5.

The nozzles in FIGS. 3, 4, 5 and 6 are Schlick Kreisl-Düse, model 121V with centralising conus, and made of austenitic stainless steel. The nozzles have been surface hardened by Kolsterising® to increase the surface hardness of the metal, in particular of the surface that in use is in contact with the liquid ortho-xylene, to a level expressed as Vickers hardness number of at least 600, preferably at least 1000.

Figure 7:
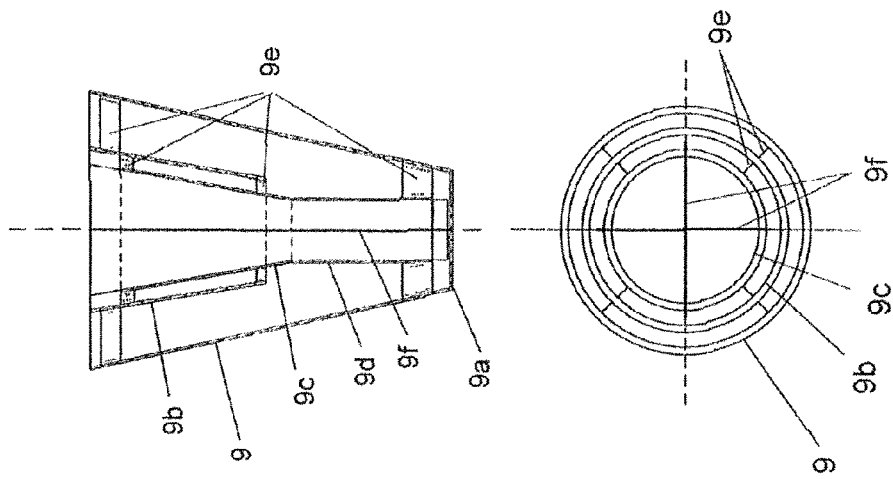
FIG. 7 shows the lower sieve basket provided with quieting vanes shown in FIG. 2 in more detail. The vanes reduce the turbulence in the air before it is mixed with the ortho-xylene.

FIG. 7 shows on top a longitudinal cross section and below that a view looking down into the lower sieve basket with the turbulence quieting vane system that is provided in the air stream upstream of the introduction of the ortho-xylene. The wing shaped circular vane system reduces the turbulence in the air as it is blown towards the ortho-xylene spray nozzle system. The sieve basket (9) itself consists of a shell, having the shape of a reversed truncated cone, with the walls and the bottom plate (9a) being perforated to let the gas pass but absorb any shock waves. We have found it advantageous for the shock wave absorption performance of the lower and/or the upper sieve basket(s), that the velocity of the gas passing the sieve basket perforations is higher than upstream and downstream thereof. Inside of the sieve basket (9) are provided concentric cone-shaped vanes (9b, 9c([two are shown]. The outer cone-shaped vane (9b) is supported at the top by connections (9e) [four shown] to the upper part of the sieve basket (9). A smaller inner cone-shaped vane (9c) is supported at the top by connections (9e, 4 shown) to the outer cone-shaped vane (9b), as well as at the bottom end of the outer cone-shaped vane (9e, 4 shown). A pipe (9d) is connected to the smallest diameter end of the inner cone-shaped vane (9c) and reaches down to the bottom perforated plate (9a) of the sieve basket. Along the length of the pipe (9d) and the inner cone-shaped vane (9c) connected thereto, further cross-shaped vanes (9f) are provided to avoid flow instabilities around the centre longitudinal axis of the sieve basket. The concentric cone-shaped vanes (9b, 9c) in the upper part of the sieve basket, together with the pipe (9d) improve the flow profile such that differences in gas flows across the upper cross section of the sieve basket are minimised. The lower part of FIG. 7 is a top view of the sieve basket (9), illustrating how the cone-shaped vanes (9b, 9c) are provided concentrically to the sieve basket (9) itself, supported by connections (9e), and how the cross-shaped vanes (9f) are provided inside the volume of the inner cone-shaped vane (9c).

Figure 8:
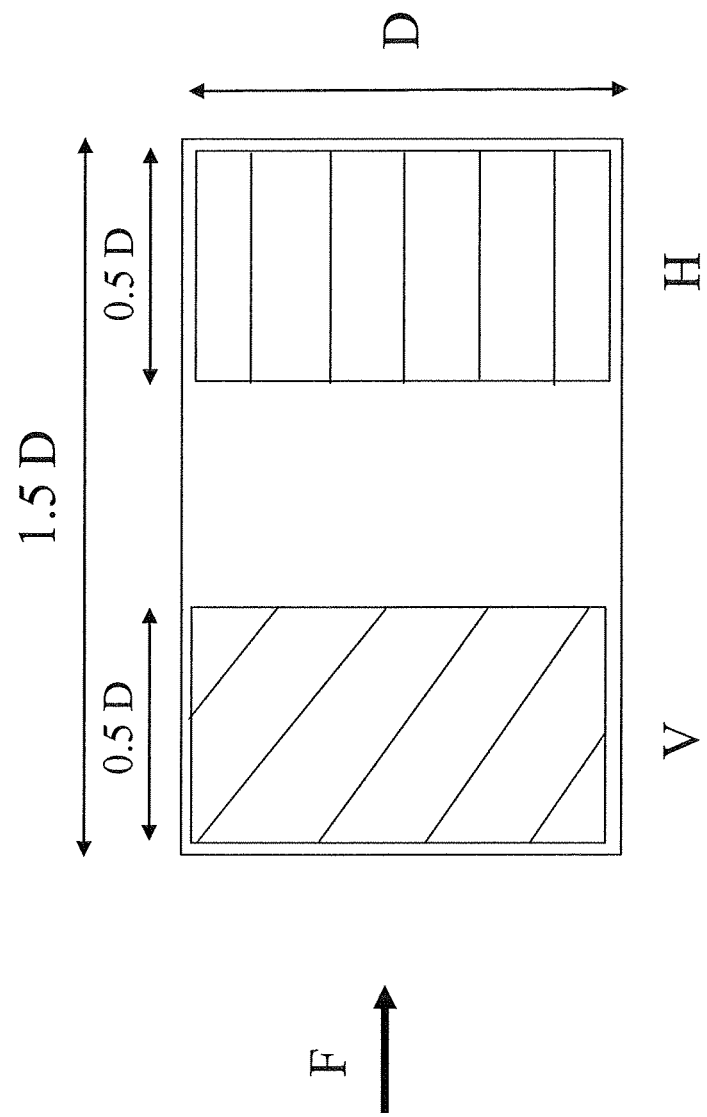
FIG. 8 shows the static mixer part of the homogeniser that is used to ensure a uniform mixture of air and ortho-xylene prior to introduction into the reaction section shown in FIG. 1.

FIG. 8 shows the homogenising static mixer through which the mixture of air and ortho-xylene passes, with flow direction F, before introduction into the reactor. FIG. 8 shows a first stage V in which the mixture moves from bottom to top and top to bottom through a vertical flow mixing element and a second stage H in which it passes from side to side through a horizontal flow mixing element. The vanes provided in the homogeniser aid in ensuring a uniform mixture of air and ortho-xylene in the mixture that is fed to the reactor. The preferred dimensions of the flow mixing elements, and their relative locations, are indicated in FIG. 8 relative to the pipe diameter D.

The phthalic anhydride produced according to the invention may be used for esterification with an alcohol or an alcohol mixture to produce the corresponding di-ester. Suitable esterification processes are disclosed in WO 2005/021482, WO 2006/012989 and in pending patent applications U.S. Ser. No. 60/906,732 and U.S. Ser. No. 60/906,797. The alcohol may be a secondary alcohol, such as isopropanol, but is preferably a primary alcohol. Suitable primary alcohols are $C_1$-$C_{13}$ primary alcohols, and may be branched or unbranched, such as methanol, ethanol, n-propanol, n-butanol, isobutanol, isohexanol, isoheptanol, iso-octanol, 2-ethyl-hexanol, isononyl alcohol, 2,4-dimethyl heptanol, normal decanol, isodecanol, isoundecyl alcohol, 2-propyl heptanol, undecyl-dodecyl alcohol, isotridecyl alcohol and mixtures thereof. Dimethylphthalate and diethylphthalate are preferred products for personal care applications. The phthalates with alkyl chains having 4 or more carbon atoms, up to 13, are used as plasticizers for polyvinyl chloride (PVC). The process of the invention is suitable for producing all these phthalates, in particular those produced from alcohols or alcohol mixtures having an average of 8 to 10 carbon atoms, especially those having an average of approximately 9 carbon atoms, such as those designated as DOP, DINP, DIDP and DTDP. Di-isononyl phthalate (DINP) is highly preferred as a PVC plasticiser, and so is di-isodecyl phthalate (DIDP). Also suitable is di-propylheptyl phthalate (DPHP) These higher molecular weight phthalates provide a higher permanence in the flexible PVC end product compared to the lower molecular weight equivalents such as di-2-ethylhexyl phthalate (DEHP or also called DOP). Di-isotridecyl phthalate (DTDP) is preferred in low volatility applications such as special purpose Wire and Cable manufacture. These phthalate esters may further be hydrogenated to form their corresponding 1,2-cyclohexane dicarboxylic acid esters, such as e.g. di-isononyl dicyclohexanoate, as disclosed in WO 2003/029339 The latter hydrogenation step may be performed by techniques known in the art, such as by using the processes described in EP 1042273 or WO 2004/046078.

The alcohols used in the esterification may be so-called oxo-alcohols, produced by the hydroformylation of olefins, when necessary followed by hydrogenation of the aldehyde intermediate. Suitable processes for hydroformylation are disclosed in WO2005/058787 or in copending applications PCT/EP2008/053783 and PCT/EP2008/053718, and suitable processes for aldehyde hydrogenation are disclosed in WO2005/058782.

The hydroformylation and hydrogenation processes for producing the oxo-alcohols, as well as the process for hydrogenating the phthalate ester, need a source of hydrogen. The hydrogen may be supplied from a variety of sources, such as but not limited to refinery processes, partial oxidation (PDX) of various starting materials, steam reforming, autothermal reforming (ATR) or the like. One of the potential sources of hydrogen is a refinery process called catalytic reforming, sometimes also called a Platforming process, wherein a refinery liquid stream, typically a naphtha or equivalent containing primarily naphthenes and/or paraffins in the C6 to C11 range, is converted to a product rich in aromatics over a heterogeneous precious metal chloride catalyst. These kind of processes are often known as a "Powerformer" or "Powerforming" processes (developed by Exxon), or as Continuous Catalyst Regeneration (CCR) processes (as e.g. offered by UOP and IFP). The hydrogen from such a catalytic reforming processes contains small amounts of chloride, at a level in the order of 1-10 ppm by volume. It is believed that most of this chloride is present as hydrogen chloride, which is more readily detected by direct gas analysis and at a typical level of 4-8 ppmv. It is however suspected that, in addition, also organic chlorides may be present, and possibly even at similar levels as the HCl. Many hydrogen consuming processes are sensitive to chloride poisoning, and a chloride removal step is typically foreseen to remove HCl from the catalytic reforming hydrogen byproduct, most typically down to a level of at most 1 ppmv. A typical chloride removal step is the adsorption of chloride over activated alumina, such as alumina 9139A from UOP, CI-750 and CI-760 from BASF, Alcoa 760 from Alcoa, Puraspec from Johnson Matthey, over ZnO such as members of the Süd-Chemie Actisorb C1 series, e.g. C1 13, and/or over a molecular sieve, such as type CLR-454 obtainable from UOP or Unimol types from Unicat.

Some of the typical process steps in the production of the oxygenates, such as the alcohols, disclosed herein, may however be particularly sensitive to chloride poisoning, such as a copper chromite hydrogenation catalyst used for aldehyde hydrogenation. The alcohol production process may also employ a hydroformylation catalyst cycle comprising a closed loop with minimal purge, in particular an aqueous closed loop, such as with several of the techniques discussed herein and/or disclosed in our co-pending patent applications. Organic chlorides may become again converted to HCl in these processes. The traces of chloride coming with the hydrogen from a source such as a catalytic reforming may therefore build up in any of these aqueous loops to levels where corrosion due to chloride may become problematic, and/or where the chloride acts as a poison to the chemistry of the hydroformylation catalyst cycle, such as in a preforming step. The hydrogen from the catalytic reforming unit as feed to the alcohol production process therefore may need to be cleaned up to a lower level of chloride than for other hydrogen consuming processes, preferably to a level of at most 0.1 ppmv and more preferably at most 0.02 ppmv of chloride. We have found that the catalytic reforming hydrogen may also contain organic chloride compounds, at a concentration up to 10 ppm volume. Further we have found that organic chloride compounds are more difficult to remove by adsorption on the conventional adsorbents. Organic chlorides may therefore more easily pass through the adsorbent bed and still may cause problems in the alcohol production process. In addition, an activated alumina adsorbent may also convert part of the HCl in the hydrogen to organic chloride compounds. The activated alumina may react with HCl to form $AlCl_3$. This $AlCl_3$ is a catalyst for the formation of organic chlorides, and also for polymerising trace olefins in the hydrogen stream to form heavier components, sometimes referred to as "green oil". Organic chlorides are more difficult to detect, and typically do not show on the conventional chloride analytical methods, such as the well known Dräger tube.

We have found that an alkali treated molecular sieve, more particularly an alkali treated zeolite, is less prone to producing organic chlorides and performs much better in such chloride removal service, also adsorbing organic chloride compounds, while capable of reaching chloride loadings of up to about 20-22% wt on the adsorbent, expressed on a dry and chloride-free basis. We prefer to use a chloride adsorbent based on an alkali-treated zeolite, more particularly a zeolite, having a pH of at least 10, preferably 11, when measured in slurry. The adsorbent may comprise other components such as magnesium aluminosilicate, and binder material, and may be in the form of spheres or extrudates. An example of a suitable alkaline zeolite is product NB 316 from CLS Industrial Purification, containing from 70-90% wt of zeolite and sodium oxide and from 10-30% magnesium aluminosilicate and having a body centre cubic crystal structure, a pH of 11, a nominal pore size of 10 Angstroms, and a surface area of 630 m2/g. The product is available as 1.6 mm diameter (1/16") spheres or as 1.6 mm (1/16"), 3.2 mm (1/8") or 4.8 mm (3/16") diameter cylinders. The zeolite of the adsorbent may be of mineral origin, or may be synthetic. The zeolite may have one single crystal structure, or be a mixture of zeolites with different crystal structures. We prefer to use a mixture of faujasite, having larger 12-ring pores, and Linde Zeolite A, which as smaller 8-ring pores. The adsorbent preferably comprises a binder material in addition to the zeolite, but could be binderless. Clay is a suitable binder material, such as chlorite. The adsorbent may be formulated from fresh zeolite, or may be based on a waste byproduct from a different process using a suitable zeolite as catalyst or adsorbent material, preferably after regeneration such as by oxidative regeneration. We prefer to use an adsorbent having a large surface area, of at least 300 m$^2$/g, preferably at least 400 m$^2$/g, more preferably at least 450 m$^2$/g, typically 488 m$^2$/g. Higher surface areas are also suitable, such as 500 m$^2$/g or 600 m$^2$/g and above. The activity and capacity of the adsorbent is preferably increased by treatment with an alkali solution, typically containing NaOH, Ca(OH)$_2$, KOH or a mixture thereof.

We prefer that only the hydrogen supply to the more sensitive consumers is treated with the alkali treated molecular sieve, so that the amount of generated spent adsorbent can be minimised. The catalytic reforming hydrogen going to the less sensitive consumers may preferably undergo only the conventional cleanup. When an activated alumina adsorbent is used for this conventional cleanup, we prefer to withdraw the hydrogen for treatment with the alkali treated molecular sieve upstream of the activated alumina adsorbent, so that the amount of organic chlorides in the hydrogen to be treated with the alkali treated molecular sieve is minimised. What is described here for hydrogen from catalytic reforming processes, is equally applicable to hydrogen from other sources that may contain chlorides for instance because of chloride being present in at least one their feedstocks.

The applicants observed, when operating a mixing system for ortho-xylene with air wherein the spray nozzles were made of regular unhardened stainless steel, and teflon tape was used to seal the connections between the spray nozzles and the lances, that cavitation and wear were causing damage to the spray nozzles, leading to spray nozzle performance deteriorating over time, causing hot spot development on the oxidation catalyst in the downstream reactor, which, at loadings of about 85, 90 grams/Nm$^3$ or higher, were leading to ignition of the gas mixture by backfire and to deflagrations occurring in the vaporizer, the homogenising section and/or the reactor section, each time leading to process downtime. It was found that by employing the features of the current invention, in particular spray nozzles that are made of Kolsterized austenitic stainless steel, and seal rings made of annealed red copper, damage to the spray nozzles could be much reduced, and the phthalic anhydride process could be operated with much longer runlengths, because deflagrations occurred with a much lower frequency and could essentially be avoided.

Phthalic anhydride (PAN) has a melting point of about 131° C. and is solid at ambient temperature. It can therefore be converted from its liquid or molten form in the production process into solid flakes, and be stored, sold and handled commercially as flakes. In this case, it is not unusual that the PAN flakes are melted before the molten PAN is pumped into the consuming process. PAN is however very often stored, sold, transported and handled in its molten form, as a hot liquid typically at temperatures of 160° C. or above. Esterification processes producing phthalate esters are often supplied with molten PAN. This is even more common where the PAN production facility is located in the proximity of the ester production facility.

The molten PAN exhibits a vapour pressure, and the vapour spaces in the equipment containing PAN therefore contain PAN vapours. Upon cooling of equipment items containing PAN vapours, the PAN may solidify as snow-like flakes. This may for instance occur in overhead systems, in vents of process equipment and/or storage vessels to the atmosphere, and in vapour clouds originating there from. The latter is undesirable from an environmental aspect, and may raise concerns of industrial hygiene because of possible effects of PAN on humans via contact with skin or by inhalation. Inside the equipment, it gives rise to concerns for plugging of equipment lines, possibly leading to vacuum pulling on storage tanks which may lead to tank collapsing.

We have found that these concerns can be significantly reduced by providing, at appropriate locations in overhead systems and vent lines, a solids knock-out volume wherein the vapour velocity is suddenly dropped for a short period. The effect is that a portion, if not all, of the flakes in the vapour stream are not carried further at the lower vapour velocities and collect at the bottom of the knock-out volume. The collected solids may then be recovered from the knock-out volume bottom at an appropriate time and be reintroduced into the process. In atmospheric vent lines, for instance, the knock-out volume may be provided by a "snow box", i.e. a wider piece of elbow or T-shaped pipe at the bottom of the vent stack, equipped with a manually removable cover on the side of the bottom volume or on one of the T-ends, through which the flakes can be removed t regular intervals.

We have found that these "snow boxes" and solids knock-out volumes are an interesting provision in the PAN production facility, as well as in the handling, storage and transportation facilities for PAN as a hot liquid, and also in the PAN consumption process facilities, such as a phthalate ester production plant.

We have found that the better locations to provide such solids knock-out volumes are the locations in the equipment where the vapors are cooler, typically also where the lower pressures occur. At these locations, the amount of solids that are formed and may be recovered is typically higher.

Having now fully described this invention, it will be appreciated by those skilled in the art that the invention can be performed within a wide range of parameters within what is claimed, without departing from the spirit and scope of the invention.

The invention claimed is:

1. A system for mixing ortho-xylene with an oxygen-containing gas, which system comprises an ortho-xylene evaporator vessel connected to be fed with a stream of oxygen-containing gas and provided with a lance projecting into the stream of oxygen-containing gas, which lance is provided with a metal spray nozzle adapted to inject droplets of liquid ortho-xylene into the stream of oxygen-containing gas concurrently with the direction of flow of the stream of oxygen-containing gas, in which the metal at the surface of the spray nozzle, that in use is in contact with the liquid ortho-xylene, is hardened steel obtained by a surface hardening treatment and has a hardness expressed as a Vickers hardness number of at least 200.

2. The system according to claim 1 in which the hardness of the metal is at least 600.

3. The system according to claim 1 in which the surface hardening treatment is by nitriding the spray nozzle surface.

4. The system according to claim 1 wherein the metal is corrosion resistant steel.

5. The system according to claim 4 wherein the metal at the surface of the spray nozzle is hardened austenitic stainless steel.

6. The system according to claim 1 in which the spray nozzle has a longitudinal symmetry axis and the direction of the longitudinal symmetry axis of the spray nozzle is parallel to the direction of flow of the gas stream.

7. The system according to claim 1 in which the spray nozzle has a longitudinal symmetry axis and the direction of the longitudinal symmetry axis of the spray nozzle is at an angle to the direction of flow of the gas stream.

8. The system according to claim 1 which comprises a plurality of said lances, forming a spray nozzle system.

9. The system according to claim 1 in which the hardness of the metal is at least 1200.

* * * * *